United States Patent [19]

Scheuermann

[11] Patent Number: 4,784,128
[45] Date of Patent: Nov. 15, 1988

[54] SHOULDER-JOINT BANDAGE

[75] Inventor: Rainer Scheuermann, Raisdorf, Fed. Rep. of Germany

[73] Assignee: Bauerfeind GmbH & Co., Kempen, Fed. Rep. of Germany

[21] Appl. No.: 135,148

[22] Filed: Dec. 18, 1987

[30] Foreign Application Priority Data

Dec. 18, 1986 [DE] Fed. Rep. of Germany ... 8633843[U]
Feb. 12, 1987 [DE] Fed. Rep. of Germany ....... 3704288

[51] Int. Cl.$^4$ ............................................... A61F 13/10
[52] U.S. Cl. ...................................... 128/165; 128/77; 2/310; 2/45; 604/388
[58] Field of Search ................. 128/155, DIG. 19, 78, 128/77, 165, 157, 171, 169, 149; 2/44, 45, 310; 604/308, 388

[56] References Cited

U.S. PATENT DOCUMENTS

| 759,256 | 5/1904 | Ferneau | 2/310 |
|---|---|---|---|
| 3,000,378 | 9/1961 | Zieman | 128/165 |
| 3,338,236 | 8/1967 | McLeod | 2/44 |
| 4,353,133 | 12/1982 | Williams | 2/45 |
| 4,598,703 | 7/1986 | Lindemann | 128/77 |
| 4,644,939 | 2/1987 | Coleman | 2/45 |

FOREIGN PATENT DOCUMENTS

| 0198482 | 10/1986 | European Pat. Off. | 128/77 |
|---|---|---|---|
| 328915 | 11/1920 | Fed. Rep. of Germany | 604/308 |
| 20530 | 8/1918 | France | 128/77 |

Primary Examiner—David Wiecking
Assistant Examiner—Huong Q. Pham
Attorney, Agent, or Firm—Herbert Dubno

[57] ABSTRACT

A shoulder-joint bandage having an elastic sleeve and a pair of belts which extend helically around the sleeve in opposite senses from the distal end thereof to then run along opposite lateral edges of a cap of the sleeve overlying the shoulder. The belts cross again behind the back of the patient and one belt passes around the other arm through the armpit and joins the other belt, e.g. at a buckle permitting longitudinal adjustment of the belts.

10 Claims, 2 Drawing Sheets

SHOULDER-JOINT BANDAGE

FIELD OF THE INVENTION

My present invention relates to a shoulder-joint bandage and, more particularly, to a bandage which can be applied for a variety of purposes to secure the shoulder joint and the upper arm regions with respect to the acromion or subacromial structures.

BACKGROUND OF THE INVENTION

It is often desirable to provide for a postoperative protection of the shoulder joint or the shoulder-corner joint, e.g. in the case of surgical intervention for rotator-cuff rupture, painful shoulder stiffness, subcapital humerus fracture, shoulder luxation, collarbone or shoulder dislocation, or a like malady, to provide a bandage for the shoulder which can reduce the pain and promote a healing process.

Because of the anatomical uniqueness of the shoulder region, a versatile shoulder bandage has not been developed for such purposes up to now.

OBJECT OF THE INVENTION

It is, therefore, the object of this invention to provide a bandage which can be utilized for the bandaging of a shoulder joint and which can be used in a wide variety of maladies to provide a secure retention of the shoulder joint.

SUMMARY OF THE INVENTION

This object and others which become apparent hereinafter can be attained, in accordance with the present invention, in a shoulder-joint bandage for relieving pain as a result of shoulder-joint surgery and for shoulder malfunction which comprises a sleeve of elastic material receiving one of the upper arms of a patient and having a distal edge remote from the respective shoulder joint of the patient and means composed of elastic material forming a cap at a proximal end of the sleeve overlying the shoulder and thus the shoulder joint of the patient. The cap is provided at a proximal end of the sleeve and the sleeve can have a proximal edge at this proximal end, which is spaced from the distal edge across the length of the sleeve and is located on the underside of the latter. The cap has lateral edges extending to an upper portion of the cap from the proximal edge along opposite sides of the sleeve.

According to the invention, a first flexible belt, which can be elastic, but preferably is substantially inelastic, extends generally helically in one rotational sense from an upper part of the distal edge around the sleeve toward the shoulder joint and then along one of the lateral edges. An extension portion of this first belt then extends free from attachment to the sleeve across the back of the patient, running below the armpit of the other arm of the patient. The first belt is secured to the sleeve where the first belt extends therearound.

In addition, the bandage of the invention comprises a second flexible belt which can be elastic, but preferably is substantially inelastic, extending generally helically in an opposite rotational sense from the upper part of the distal edge of the sleeve toward the shoulder joint and crossing the first belt on the sleeve preferably at the underside of the latter.

The second belt then extends along the other lateral edge of the cap previously described.

An extension portion of the second belt, free from attachment to the sleeve, continues from the portion of the second belt which runs along the other lateral edge across the back of the patient to again cross the first belt and is connected to the first belt at a location remote from the sleeve. Where the second belt extends around the sleeve, it may be secured thereto and is secured thereto at least along the other lateral edge and at the upper part of the distal edge.

The tubular sleeve of the invention thus engages over the upper arm of the patient, is formed with the cap at this proximal end which overlies and encloses the shoulder, and extends from the shoulder joint toward the elbow of the patient.

The edge spaced from the cap, i.e. the distal edge described previously, serves as the starting point or the initial anchorage of the two flexible belts which wind helically in opposite senses around an elastic sleeve and are secured to the latter also lying the opposite lateral edges formed by the cap, running upwardly along these lateral edges from a crossover of the belts on the underside of the sleeve.

Both belts then run free from attachment to the sleeve across the back of the patient and cross once again, before being joined to form a loop which engages below the shoulder joint of the other arm in the armpit thereof. These free portions of the belts are referred to herein as extension belts.

According to the invention, at least the material from which the tubular sleeve is made is longitudinally elastic and indeed, as noted, both the sleeve and cap can be composed of longitudinally elastic material and the belts, of course, can be formed of longitudinally elastic material as well.

According to a feature of the invention, the two belts are connected for longitudinal adjustability by appropriate means such as a buckle or the like.

To increase the comfort of the patient, a cushion member, e.g. of tubular construction, can be slidable along the first belt and can engage in the armpit and under the other arm of the patient.

Where the belts engage the sleeve or its cap and are affixed thereto, the sleeve or cap can be formed with pockets through which the belts can pass.

Advantageously, the belts are joined together, e.g. by stitching, where they cross over along the back of the patient.

It has been found to be advantageous, moreover, to provide the sleeve and/or cap with a pocket in which one or more wads or pads of silicone rubber surgical cotton, gauze pads or the like can be inserted to provide local pressure upon the acromion process or the acromiol-clavicular joint.

BRIEF DESCRIPTION OF THE DRAWING

The above and other objects, features and advantages of the present invention will become more readily apparent from the following description, reference being made to the accompanying drawing in which.

SPECIFIC DESCRIPTION

Figure 1:
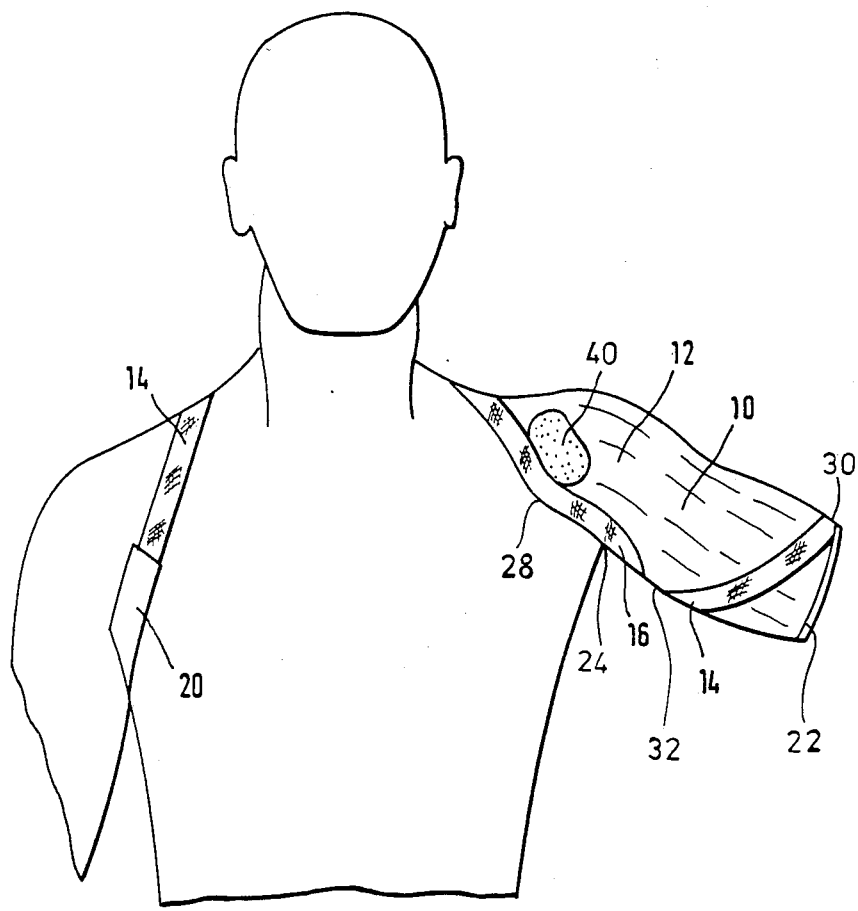
FIG. 1 is a front elevational view showing the shoulder bandage of the invention on a patient.

The shoulder-joint bandage illustrated in the drawing comprises a tubular member or sleeve 10 composed of an elastic material and preferably knitted in one piece from a longitudinally elastic material which can be provided in one piece with a cap 12 enclosing the shoulder and reaching over the latter, the cap being likewise composed of elastic material.

The sleeve 10 has a distal edge 22 which lies close to the elbow of the patient and thus is remote from the cap 12 which is formed on the proximal end of the sleeve 10. The sleeve 10 below the cap, i.e. at 24 in the armpit of the bandaged shoulder, has a proximal edge from which a pair of lateral edges 26 and 28 of the cap extend upwardly.

The shoulder bandage of the invention also comprises two extension belts which may e formed in one piece but are, for convenience in description, treated separately.

Figure 2:
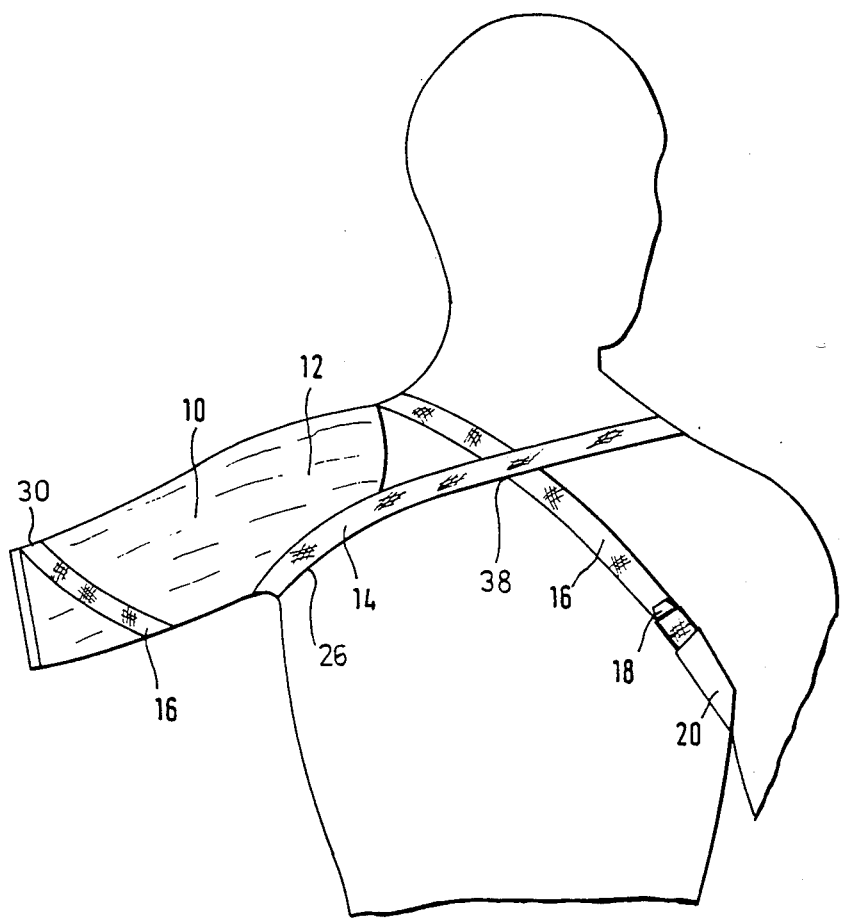
FIG. 2 is a rear elevational view of the bandage.
Figure 4:
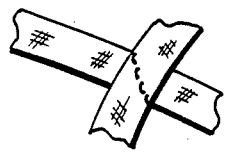
FIG. 4 is an elevational view showing the back crossover of the belts in the case in which they are stitched together.

The first of these belts 14 extends from an upper region 30 of the distal edge 22 helically around the sleeve 10 and thence along one of the lateral edges 26 of the cap to pass across the back of the patient (FIG. 2), and loop over the opposite shoulder of the patient and under the armpit of this other shoulder. The helical path of the first belt extends initially forwardly (FIG. 1) and then below the sleeve 10 to cross at 32, the other belt 16, whereupon the first belt 14 passes upwardly along the edge 26. At 30 and along the edge 26, the first belt may be secured to the sleeve, e.g. by passing through a pocket 4 formed by sewing a strip 36 onto the sleeve 10 or by knitting the sleeve 10 with such a pocket.

The second extension belt 16 is likewise fastened at 30 to the sleeve 10 and passes helically in the opposite sense, i.e. initially rearwardly (FIG. 2), around the sleeve 10 to cross at 32 the belt 14 and then passes upwardly along the other lateral edge 28 of the cap 12 being secured, e.g. in a pocket 34 therealong.

The extension belt 16 then passes, free from attachment to the sleeve, across the back of the patient (FIG. 2) forming a second crossover at 38 with the first belt 14 before being secured to the free end of the belt 14 which has passed through the armpit of the patient by a buckle 18 which allows longitudinal adjustment of the belts and can permit the bandage to be tightened. Any conventional buckle utilized for joining the belts or straps of a prosthesis or bandage may be used for this purpose and hence the buckle has not been shown in great detail.

The first belt 14 is also provided with a tubular cushion 20 where this belt passes through the armpit of the patient to prevent any discomfort of the patient by this belt and to distribute the pressure thereof.

Figure 3:
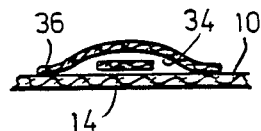
FIG. 3 is a cross section through a portion of the sleeve or cap showing a belt passing through a pocket of the sleeve or cap.

The pockets 34 illustrated in FIG. 3 can be used wherever the belts 14 and 16 are to be connected to the sleeve 10, e.g. along the edges 26 and 28 and in the region 30. Of course, if desired, the belts 14 and 16 can be stitched to the sleeve 10 in these regions.

A further pocket 40 can be provided at the region of the acromion process or at the acromiol-clavicular joint to receive a silicone pad or wad, a surgical cotton pad or wad or a gauze pad or wad to apply pressure in this region.

As will be apparent, the shoulder bandage of the invention permits the bandaging of the shoulder region in a simple and effective manner.

The outwardly rotating effect of the first extension belt 14 is balanced by the counterrotation of the second extension belt 16. Intentional outward and inward rotation and both abduction and elevation can be promoted or permitted by the belts 14 and 16.

The second belt 16 in the region extending along the edge 28 can support the subacromial or acromial-clavicular joint.

It will be understood that the shoulder-joint bandage of the invention can be made available in a variety of standard sizes for use with a variety of patients.

It is applied by inserting the patient's upper arm through the sleeve from the proximal end thereof and buckling the straps at the back of the patient behind the armpit region of the other arm.

I claim:

1. A shoulder-joint bandage for relieving pain as a result of shoulder-joint surgery and malfunction, comprising:
   a sleeve of elastic material receiving one of the upper arms of a patient and having a distal edge remote from the respective shoulder joint of the patient and a cap at a proximal end of said sleeve overlying the shoulder joint whereby said sleeve has a proximal edge at said proximal end spaced from said cap and said cap has lateral edges extending from said proximal edge to an upper portion of said cap; and a first flexible belt and a second flexible belt;
   said first flexible belt extending generally helically around said sleeve in a first direction from an upper part of said distal edge toward said shoulder joint, and along one of said lateral edges, said first belt extending from said sleeve across the back of the patient, running below the armpit of the other arm of the patient and being secured to said second belt;
   said second flexible belt extending generally helically around said sleeve in an opposite direction from said first direction from said upper part of said distal edge toward said shoulder joint and crossing said first belt on said sleeve, and along the other of said lateral edges, said second belt extending free from said sleeve across the back of the patient to again cross said first belt, being connected to said first belt at a location remote from said sleeve, and being secured to said first belt.

2. The shoulder-joint bandage defined in claim 1 wherein the material of said sleeve is longitudinally elastic.

3. The shoulder-joint bandage defined in claim 1, further comprising a length-adjustable member interconnecting said first and second belts.

4. The shoulder-joint bandage defined in claim 1, further comprising a cushion member on said first belt shiftable therealong and adapted to engage beneath the other arm of the patient.

5. The shoulder-joint bandage defined in claim 1 wherein at least part of said sleeve is formed with pockets receiving said first and second belts.

6. The shoulder-joint bandage defined in claim 5 wherein said pockets are provided in said cap.

7. The shoulder-joint bandage defined in claim 5 wherein said pockets are provided in a portion of said sleeve other than said cap.

8. The shoulder-joint bandage defined in claim 1 wherein said belts are sewed together where they cross again.

9. The shoulder-joint bandage defined in claim 1 wherein said cap is provided with a pad-receiving pocket.

10. The shoulder-joint bandage defined in claim 1 wherein said belts are longitudinally elastic and stretchable.

* * * * *